(12) United States Patent
Allgeier et al.

(10) Patent No.: US 7,737,294 B2
(45) Date of Patent: Jun. 15, 2010

(54) PROCESS OF HYDROCYANATION OF UNSATURATED CARBOXYLIC ACID DERIVATIVES

(75) Inventors: Alan Martin Allgeier, Wilmington, DE (US); Christian Peter Lenges, Wilmington, DE (US)

(73) Assignee: Invista North America S.A R.L., Wilmington, DE (US)

( * ) Notice: Subject to any disclaimer, the term of this patent is extended or adjusted under 35 U.S.C. 154(b) by 1372 days.

(21) Appl. No.: 10/935,819

(22) Filed: Sep. 8, 2004

(65) Prior Publication Data

US 2005/0059737 A1   Mar. 17, 2005

Related U.S. Application Data

(60) Provisional application No. 60/501,927, filed on Sep. 11, 2003.

(51) Int. Cl.
C07C 255/03 (2006.01)
(52) U.S. Cl. ..................................................... 558/441
(58) Field of Classification Search ............... 558/441
See application file for complete search history.

(56) References Cited

U.S. PATENT DOCUMENTS 2,411,593 A    11/1946  Routson
2,426,056 A    8/1947   Rust
5,461,036 A *  10/1995  Otake et al. ................... 514/46

FOREIGN PATENT DOCUMENTS

| GB | 1 104 115 | 2/1968 |
| WO | WO 95/14659 | 6/1995 |
| WO | WO 99/06358 | 2/1999 |
| WO | WO 02/40440 | 5/2002 |

OTHER PUBLICATIONS

Goertz, W. et al, "Application of Chelating Diphosphine Ligands in the Nickel-catalyzed Hydrocyanation . . . ", Chemical Communications, vol. 16, 1997, pp. 1521-1522 (XP002318778.
Tukao, Yugi, et al., Journal of Health Sciences, 2003, 49(1), pp. 88-90.

* cited by examiner

*Primary Examiner*—James O Wilson
*Assistant Examiner*—Ebenezer Sackey

(57) ABSTRACT

The present invention is directed to compositions of specific carboxylic acid, fatty acid or oil derivatives containing nitrile groups and methods of their preparation. The preparation involves a hydrocyanation reaction. A method of hydrgenating the nitrile containing carboxylic acid acids obtained by above hydrocyanation to produce amine containing carbixylic acids is also disclosed in this invention.

1 Claim, No Drawings

PROCESS OF HYDROCYANATION OF UNSATURATED CARBOXYLIC ACID DERIVATIVES

FIELD OF THE INVENTION

This invention is related to the field of hydrocyanation of olefins and in particular, hydrocyanation of unsaturated carboxylic acids, fatty acids and oils comprising these acids.

BACKGROUND OF THE INVENTION

Unsaturated fatty acids and oils comprising unsaturated carboxylic acids are attractive substrates for a variety of applications such as monomers for polymeric materials, as ingredients in composites, as lubricants or as fine chemicals. These materials are especially attractive since they are based on natural sources and therefore offer an environmentally and ecologically responsible route to useful chemicals. Significant effort has been devoted toward further transformations of these long chain unsaturated fatty acids to arrive at new, functional materials.

Towards this end the current invention provides a process of hydrocyanation of unsaturated and/or poly-unsaturated carboxylic acids, especially fatty acids and/or oils comprising these fatty acids to form the corresponding fatty acid/oil nitrile products. In case of the oils, typical examples are natural occurring oils, for example soybean oil. The products can be mononitriles, dinitriles and/or polynitriles. Furthermore these nitriles can be converted to the corresponding methylene-amines via a hydrogenation reaction.

Unsaturated carboxylic acids, and especially fatty acids and their derivatives containing nitrile groups are of interest as lubricants, surfactants or precursors to a variety of useful molecules. Typical examples of unsaturated fatty acids, which are naturally occurring, include mono- or polyunsaturated carboxylic acids, such as oleic acid, lauroleic acid, myristoleic acid, palmitoleic acid, linoleic acid, and arachidonic acid. Naturally occurring oils, for example soybean oil, comprise glycerin esters of these unsaturated fatty acids. Other typical useful unsaturated carboxylic acids are, for example, 3-pentenoic acid or 4-pentenoic acid.

Goertz et al. in Chem. Commun., 1521 (1997) disclosed a hydrocyanation reaction of ω-unsaturated fatty acid esters (i.e. containing a terminal olefin) using nickel phosphine catalysts. The reported yields are undesirable for commercial application. Additionally, it is known in the art that internal olefins, such as those in many naturally occurring fatty acids and esters, are more difficult to react in a hydrocyanation process than terminal olefins, such as those found in ω-unsaturated fatty acid esters.

WO 99 06358 A1 disclosed the hydrocyanation of monoethylenically unsaturated ester compounds to provide linear terminal nitrile molecules but did not disclose the hydrocyanation of carboxylic acids. Acidic compounds are known to deactivate catalysts and degrade typical hydrocyanation ligands.

Prior to the present invention, it was not known that unsaturated fatty acids or naturally occurring oils with olefinic unsaturation could be converted selectively in a hydrocyanation process to the corresponding fatty acid derivatives with nitrile groups in high yields. It was also not known that the so formed derivatives of fatty acids containing nitrile groups could be converted selectively in a hydrogenation process to the fatty acid derivatives with the corresponding amine groups. There is a need to access fatty acid derivatives, which have one or more additional functional groups, such as nitriles, amines, alcohols or carboxylic acids. In particular, derivatives of plant oils like soybean oil, which contain one or more additional functional groups are of interest.

Therefore, there remains a need for specific nitrile derivatives of unsaturated carboxylic acids, especially unsaturated fatty acids and/or oils of unsaturated fatty acids and a method to produce these compounds in general. There is also a need for derivatives of unsaturated fatty acids, which contain amine groups and for a method to produce such derivatives, which contain amine groups. These needs are met by the present invention.

SUMMARY OF THE INVENTION

The present invention is directed to compositions of specific carboxylic acid, fatty acid or oil derivatives containing nitrile groups and methods of their preparation. The preparation involves a hydrocyanation reaction. A method of hydrogenating the nitrile containing carboxylic acid acids obtained by above hydrocyanation to produce amine containing carboxylic acids is also disclosed in this invention.

The present invention is, therefore, a composition of matter of structural formula III:

(III)

and a composition of matter of structural formula V:

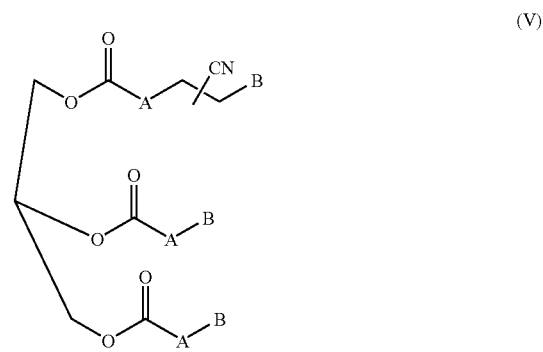

(V)

wherein:

each A is independently a group comprising one or more hydrocarbon fragments comprising —(CH$_2$)$_w$—, alkene containing fragments comprising —CH=CH—, or nitrile containing fragment comprising —(CH$_2$CHCN)— or —(CH(CN)CH$_2$)—, or a combination of two or more of these fragments in any order;

each B is independently A'-H, wherein A' is a group comprising one or more hydrocarbon fragment comprising —(CH$_2$)$_w$—, alkene containing fragment comprising —CH=CH—, or a nitrile containing fragment comprising —(CH$_2$CHCN)— or —(CH(CN)CH$_2$)—, or a combination of two or more of these fragments in any order; and wherein, w is independently 0 or a positive integer, preferably between 0 and 20.

Also disclosed is a hydrocyanation process, said process comprising converting a starting carboxylic acid in the presence of a catalyst to produce a derivative of carboxylic acid comprising one or more compounds of formula (I):

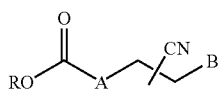
(I)

wherein:

A is a group comprising one or more hydrocarbon fragments comprising —(CH$_2$)$_w$—, alkene containing fragments comprising —CH=CH—, or nitrile containing fragment comprisings —(CH$_2$CHCN)— or —(CH(CN)CH$_2$)—, or a combination of two or more of these fragments in any order;

B is A'-H, wherein A' is group comprising one or more hydrocarbon fragment comprising —(CH$_2$)$_w$—, alkene containing fragment comprising —CH=CH—, or a nitrile containing fragment comprising —(CH$_2$CHCN)— or —(CH(CN)CH$_2$)—, or a combination of two or more of these fragments in any order; and R is H or a glycerol derivative; and wherein, w is 0 or a positive integer, preferably between 0 and 20.

Also disclosed is a process of hydrogenation comprising hydrogenating the carboxylic acid derivative to produce acid amine compounds of structural formula (II):

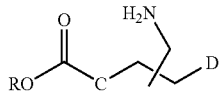
(II)

wherein

C is a group comprising one or more hydrocarbon fragments comprising —(CH$_2$)$_x$—, alkene containing fragments comprising —CH=CH—, nitrile containing fragments comprising —(CH$_2$CHCN)— or —(CH(CN)CH$_2$)—, or amine containing fragments comprising —(CH$_2$CH(CH$_2$NH$_2$)— or —(CH(CH$_2$NH$_2$)CH$_2$)—, or a combination of one or more of these fragments in any order;

D is H or C'—H wherein C' is a group comprising one or more hydrocarbon fragments comprising —(CH$_2$)$_x$—, alkene containing fragments comprising —CH=CH—, nitrile containing fragments comprising —(CH$_2$CHCN)— or —(CH(CN)CH$_2$)—, or amine containing fragments comprising —(CH$_2$CH(CH$_2$NH$_2$)— or —(CH(CH$_2$NH$_2$)CH$_2$)—, or a combination of two or more of these fragments in any order;

R is H or a glycerol derivative; and x is 0 or a positive integer, preferably between 0 and 20, wherein x is independently chosen each time it is utilized in the structure.

Notable for this invention is the use of oleic acid as the substrate to provide a nitrile derivative or a mixture of nitrile derivatives. While this invention may provide a variety of isomers described by (I), the process shows preference for the terminal nitrile, (III):

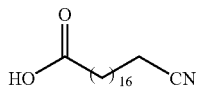
(III)

Additionally, notable is amine derivative (IV) of corresponding structure.

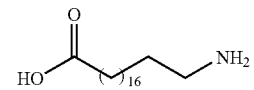
(IV)

Glycerol tri-esters with olefinic unsaturation, comprising naturally occurring plant and/or animal oils, are important feedstocks within the scope of the present invention. These glycerol tri-esters may be constructed of fatty acid fragments. Products derived from them according to the present invention can be described by formula (V) and/or (VI):

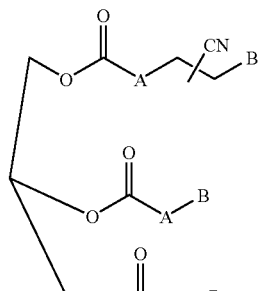
(V)

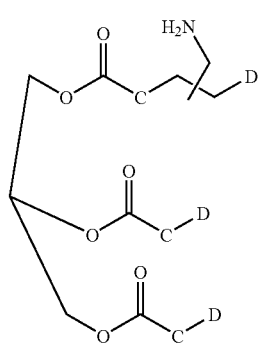
(VI)

wherein, A, B, C and D are defined as above and are of independent identity each time utilized in the structure.

These compounds are useful as organic synthesis precursors or as lubricants or in surfactant applications.

Natural glyceridic oils may also contain different degrees of unsaturation, which deviate from the stoichiometry suggested by the oleic acid derivative. Other oils useful for this invention include unsaturated plant oils such as tung oil, mono-, di-, and tri-glyceride oils such as oils from soybeans, oil seed rape, linseed, olive oil, castor oil, mustard seed oil, ground nut oil, coconut oil, corn oil, cottonseed oil, palm oil, peanut oil, safflower oil and phenolic oils such as cashew nut shell liquid.

Accordingly, it is one object of the present invention to provide carboxylic acid derivatives and especially fatty acid or oil derivatives containing nitrile groups, as well as a process for preparing them and their corresponding amines. It is another object of the present invention to provide a method for preparing such unsaturated fatty acid or oil derivatives. These and other objects will become apparent in the following detailed description.

DETAILED DESCRIPTION OF THE INVENTION

Carboxylic acids comprising one or more of the compounds of formula (I):

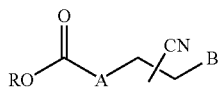

(I)

are obtained by hydrocyanation of unsaturated carboxylic acids wherein:

A is a group comprising one or more hydrocarbon fragments comprising —$(CH_2)_w$—, alkene containing fragments comprising —CH═CH—, or nitrile containing fragment comprisings —$(CH_2CHCN)$— or —$(CH(CN)CH_2)$—, or a combination of two or more of these fragments in any order;

B is A'-H, wherein A' is group comprising one or more hydrocarbon fragment comprising —$(CH_2)_w$—, alkene containing fragment comprising —CH═CH—, or a nitrile containing fragment comprising —$(CH_2CHCN)$— or —$(CH(CN)CH_2)$—, or a combination of two or more of these fragments in any order; and R is H or a glycerol derivative; and wherein, w is 0 or a positive integer, preferably between 0 and 20.

These carboxylic acid derivatives, especially these fatty acid or oil derivatives containing nitrile groups, either alone, mixtures of these, and/or isomers of these, are also useful as precursors for other useful molecules. For instance, a carboxylic acid comprising one or more compounds of formula (I) can be converted in a hydrogenation reaction to the corresponding amines comprising one or more compounds of the formula (II):

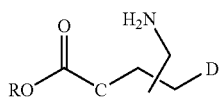

(II)

wherein

C is a group comprising one or more hydrocarbon fragments comprising —$(CH_2)_x$—, alkene containing fragments comprising —CH═CH—, nitrile containing fragments comprising —$(CH_2CHCN)$— or —$(CH(CN)CH_2)$—, or amine containing fragments comprising —$(CH_2CH(CH_2NH_2))$— or —$(CH(CH_2NH_2)CH_2)$—, or a combination of one or more of these fragments in any order;

D is H or C'—H wherein C' is a group comprising one or more hydrocarbon fragments comprising —$(CH_2)_x$—, alkene containing fragments comprising —CH═CH—, nitrile containing fragments comprising —$(CH_2CHCN)$— or —$(CH(CN)CH_2)$—, or amine containing fragments comprising —$(CH_2CH(CH_2NH_2))$— or —$(CH(CH_2NH_2)CH_2)$—, or a combination of two or more of these fragments in any order;

R is H or a glycerol derivative; and x is 0 or a positive integer, preferably between 0 and 20, wherein x is independently chosen each time it is utilized in the structure.

Notable for this invention is the use of oleic acid as the substrate to provide a nitrile derivative or a mixture of nitrile derivatives. While this invention may provide a variety of isomers described by (I), the process shows preference for the terminal nitrile, (III).

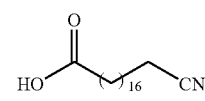

(III)

Additionally, notable is amine derivative (IV) of corresponding structure.

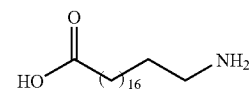

(IV)

The product is provided as a single compound or mixtures of isomers, described by (II).

Additionally, notable is the use of linoleic acid as the substrate to provide a product comprising nitrile derivatives (VII)-(VIII), and/or the amine derivatives of corresponding structure (VII-A) and (VIII-A). The products are provided as single compounds, mixtures of compounds and/or mixtures of isomers.

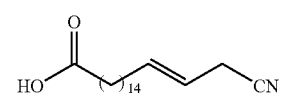

(VII)

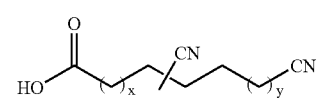

(VIII)

Glycerol tri-esters with olefinic unsaturation, comprising naturally occurring plant and/or animal oils, are important feedstocks within the scope of the present invention. These glycerol tri-esters may be constructed of fatty acid fragments. Products derived from them according to the present invention can be described by formula (V) and/or (VI):

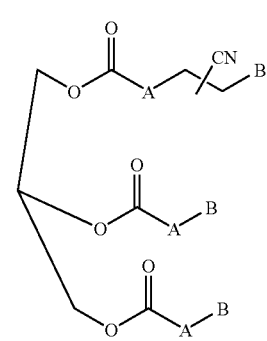

(V)

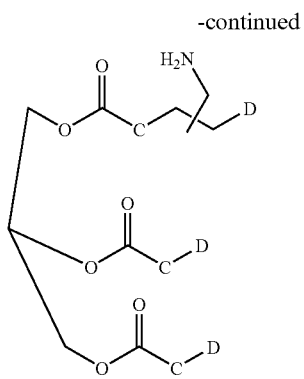

(VI)

wherein, A, B, C and D are defined as above and are of independent identity each time utilized in the structure.

These compounds are useful as organic synthesis precursors or as lubricants or in surfactant applications.

Natural glyceridic oils may also contain different degrees of unsaturation, which deviate from the stochiometry suggested by the oleic acid derivative. Other oils useful for this invention include unsaturated plant oils such as tung oil, mono, di, and tri-glyceride oils such as oils from soybeans, oil seed rape, linseed, olive oil, castor oil, mustard seed oil, ground nut oil, coconut oil, corn oil, cottonseed oil, palm oil, peanut oil, safflower oil and phenolic oils such as cashew nut shell liquid.

The inventors have discovered that unsaturated carboxylic acids, especially unsaturated fatty acids and/or oils of fatty acids can be contacted with hydrogen cyanide, in the presence of a catalyst and optionally a promoter at a temperature of about 0° C. to about 120° C. to yield carboxylic acid derivatives of the formula (I), wherein the catalyst comprises a transition metal, preferentially nickel and an organic phosphorous ligand. Further, they have discovered that compounds or mixtures described by (I) (and thus (III) and (V)) may be converted to compounds or mixtures described by (II) (and thus (IV) and (VI)) by contacting compounds or mixtures (I) with hydrogen, in the presence of a transition metal catalyst at a temperature in the range of about 50° C. to about 180° C. and a pressure in the range of of about 50 to about 5000 psig (340 to 34,480 kPa), optionally in the presence of a solvent. A simple extension of this process would encompass the use of simple fatty acid esters as the starting material, instead of fatty acids. Such fatty acid esters can be prepared via the reaction of alcohols with fatty acid oils and comprise alkyl and aryl esters. Examples of fatty acid esters include methyl oleate, methyl linoleate, ethyl oleate, butyl oleate and the like.

Thus, in one embodiment, the present invention provides a hydrocyanation method for preparing derivatives of unsaturated carboxylic acids, especially fatty acids and/or oils, which contain nitrile groups. Generally, the present method yields the acid derivative as a mixture of isomers. The mixture obtained by the present method generally does not contain the isomers in equal amounts. Instead, the method may yield one or several compounds as main products, while others are formed as by-products in varying amounts. The method can be implemented to favor one set of compounds as the main products. The set of compounds favored in this method is a function of process conditions and/or the type of catalyst or catalysts used and/or the type of ligand used in the hydrocyanation reaction and/or the use of an optional promoter in the hydrocyanation reaction. However, it is to be understood that both the individual compounds and also the mixtures thereof are within the scope of the present invention.

The method for making the compounds of the present invention involves a hydrocyanation process with the use of a ligand and a Group VIII metal or compound. Optionally, one may use a Lewis acid in the process as a promoter, and one may optionally use a solvent.

Generally, a Group VIII metal or compound thereof is combined with at least one ligand to provide the catalyst. Among the Group VIII metals or compounds, nickel, cobalt, and palladium compounds are preferred to make the hydrocyanation catalysts. A nickel compound is more preferred. A zero-valent nickel compound that contains a ligand that can be displaced by a ligand of the prior art is the most preferred source of Group VIII metal or Group VIII metal compound.

Zero-valent nickel compounds can be prepared or generated according to methods known in the art. Three preferred zero-valent nickel compounds are $Ni(COD)_2$ (COD is 1,5-cyclooctadiene), $Ni(P(o\text{-}OC_6H_4CH_3)_3)_3$ and $Ni\{P(O\text{-}o\text{-}C_6H_4CH_3)_3\}_2(C_2H_4)$; these are known in the art.

Alternatively, divalent nickel compounds can be combined with a reducing agent, to serve as a source of zero-valent nickel in the reaction. Suitable divalent nickel compounds include compounds of the formula $NiX^2_2$ wherein $X^2$ is halide, carboxylate, or acetylacetonate. Suitable reducing agents include metal borohydrides, metal aluminum hydrides, metal alkyls, Li, Na, K, Zn, Al or $H_2$. Elemental nickel, preferably nickel powder, when combined with a halogenated catalyst is also a suitable source of zero-valent nickel.

Suitable ligands for the present invention contain trivalent phosphorus atoms in which each trivalent phosphorous atom is known as phosphite or phosphinite. The ligands useful in the present invention can be bidentate ligands meaning that two trivalent phosphorus atoms in the molecule are each bonded to the same organic group, which bridges the trivalent phosphorus atoms together. The ligands in the present invention can also be multidentate with a number of phosphorous atoms in excess of 2 or of polymeric nature in which the ligand/catalyst composition is not homogeneously dissolved in the process mixture. Monodentate ligands, may be used in place of the ligands of this invention, but they provide low conversion to the desired products and suffer from poor rate and productivity. Their performance is insufficient for commercial applications. The preferred ligands in this invention are bidentate phosphite ligands.

Suitable bidentate phosphites are of the type disclosed in U.S. Pat. Nos. 5,512,695; 5,512,696; 5,663,369; 5,688,986; 5,723,641; 5,959,135; 6,120,700; 6,171,996; 6,171,997; 6,399,534, hereby incorporated by reference. Suitable bidentate phosphinites are of the type disclosed in U.S. Pat. Nos. 5,523,453 and 5,693,843, hereby incorporated by reference.

The preferred bidentate phosphite ligands are of the following structural formulae:

(XI)

(XII)

(XIII)

In formulae XI, XII and XIII, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulae XIV, XV, XVI, XVII, and XVIII

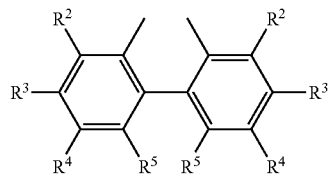

(XIV)

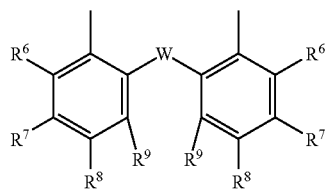

(XV)

wherein:
$R^2$, $R^3$, $R^4$, $R^5$, $R^6$, $R^7$, $R^8$, and $R^9$ are independently selected from H, $C_1$ to $C_{12}$ alkyl, and $C_1$ to $C_{12}$ alkoxy;
W is O, S, or $CH(R^{10})$; and
$R^{10}$ is H or $C_1$ to $C_{12}$ alkyl.

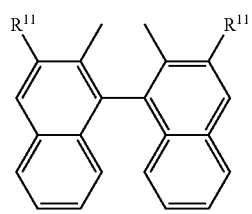

(XVI)

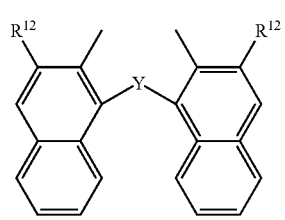

(XVII)

wherein:
$R^{11}$ and $R^{12}$ are independently selected from H, $C_1$ to $C_{12}$ alkyl, and $C_1$ to $C_{12}$ alkoxy; and $CO_2R^{13}$;
$R^{13}$ is $C_1$ to $C_{12}$ alkyl or $C_6$ to $C_{10}$ aryl, unsubstituted or substituted with $C_1$ to $C_4$ alkyl;
Y is O, S, $CH(R^{14})$; and
$R^{14}$ is H or $C_1$ to $C_{12}$ alkyl.

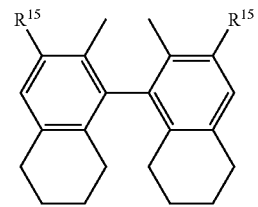

(XVIII)

wherein:
$R^{15}$ is selected from H, $C_1$ to $C_{12}$ alkyl, and $C_1$ to $C_{12}$ alkoxy; and $CO_2R^{16}$; and
$R^{16}$ is $C_1$ to $C_{12}$ alkyl or $C_6$ to $C_{10}$ aryl, unsubstituted or substituted with $C_1$ to $C_4$ alkyl.

In the structural formulae X through XVIII, the $C_1$ to $C_{12}$ alkyl, and $C_1$ to $C_{12}$ alkoxy groups may be straight chains or branched.

The ratio of ligand to active nickel can vary from a ligand to nickel ratio of about 0.5:1 to a ligand to nickel ratio of about 100:1. Preferentially the ligand to nickel ratio ranges from about 1:1 to about 4:1.

Preferably, the process of this invention is carried out in the presence of one or more Lewis acid promoters that affect both the activity and the selectivity of the catalyst system. The promoter may be an inorganic or organometallic compound in which the cation is selected from scandium, titanium, vanadium, chromium, manganese, iron, cobalt, copper, zinc, boron, aluminum, yttrium, zirconium, niobium, molybdenum, cadmium, rhenium and tin. Examples include but are not limited to $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $Cl_2Ti(OiPr)_2$, $MnCl_2$, $ScCl_3$, $AlCl_3$, $(C_8H_{17})AlCl_2$, $(C_8H_{17})_2AlCl$, $(iso-C_4H_9)_2AlCl$, $Ph_2AlCl$, $PhAlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $R^{40}Sn(O_3SCF_3)$ where $R^{40}$ is an alkyl or aryl group. Preferred promoters include $FeCl_2$, $ZnCl_2$, $CoCl_2$, $CoI_2$, $AlCl_3$, $B(C_6H_5)_3$, and $(C_6H_5)_3Sn(O_3SCF_3)$. The mole ratio of promoter to Group VIII transition metal present in the reaction can be within the range of about 1:16 to about 50:1, with 0.5:1 to about 2:1 being preferred.

The ligand compositions of the present invention may be used to form catalysts, which may be used for the hydrocyanation of unsaturated carboxylic acids, especially fatty acids or esters with or without a Lewis acid promoter.

The process comprises contacting, in the presence of the catalyst, an unsaturated carboxylic acid or oil or mixtures of one or more of these with a hydrogen cyanide-containing fluid under conditions sufficient to produce a nitrile. Any fluid containing about 1 to 100% HCN can be used. Pure hydrogen cyanide may be used.

The hydrocyanation process can be carried out, for example, by charging a suitable vessel, such as a reactor, with an unsaturated fatty acid or oil, or mixtures of one or more of these, catalyst and optionally solvent, to form a reaction mixture. Hydrogen cyanide can be initially combined with other components to form the mixture. However, it is preferred that HCN be added slowly to the mixture after other components have been combined. Hydrogen cyanide can be delivered as a liquid or as a vapor to the reaction. As an alternative, a cyanohydrin can be used as the source of HCN as known in the art.

Another suitable technique is to charge the vessel with the catalyst and, optionally, solvent and feed both the unsaturated carboxylic acid, the fatty acid or oil and the HCN slowly to the reaction mixture.

The molar ratio of unsaturated carboxylic acid/ester to catalyst can be varied from about 10:1 to about 10,000:1. The molar ratio of HCN:catalyst can be varied from about 5:1 to about 10,000:1. The process can be run in continuous or batch mode.

Preferably, the reaction mixture is agitated, for example, by stirring or shaking. The present compounds can be individually isolated from the reaction mixture, using known conventional methods, such as chromatography or fractional distillation or crystallization.

The hydrocyanation can be carried out with or without a solvent. The solvent, if used, can be liquid at the reaction temperature and pressure and inert towards the unsaturated carboxylic acid/oil and the catalyst. Examples of suitable solvents include hydrocarbons such as benzene, xylene, toluene or combinations thereof; ethers such as tetrahydrofuran (THF), nitriles such as acetonitrile, adiponitrile, or combinations of two or more thereof.

The exact temperature is dependent to a certain extent on the particular catalyst being used, and the desired reaction rate. Normally, temperatures in the range of from about 0° C. to about 200° C. can be used, the range of about 25° C. to about 120° C. being preferred.

The process can be run at atmospheric pressure. Pressures of from about 50.6 to about 1013 kPa are preferred. Higher pressures, up to 10,000 kPa or more, can be used, if desired.

The time required can be in the range of from a few seconds to many hours (such as 2 seconds to 72 hours), depending on the particular conditions and method of operation.

The present unsaturated carboxylic acid derivatives containing nitrile groups can be used alone or in mixtures with one another, for further functionalization. For example, they can be converted to their corresponding amines by hydrogenation. Thus the nitrile products either alone or as mixtures of isomers may be contacted with hydrogen in the presence of a catalyst, optionally in the presence of a solvent to yield amine compounds.

During the hydrogenation process the feed (i.e. compounds described by (I) either alone or in mixtures of isomers) is contacted with hydrogen. The mole ratio of hydrogen to feed is not critical as long as sufficient hydrogen is present to produce the desired derivatives described by (II). Hydrogen is preferably used in excess. Hydrogen pressures are generally in the range of about 340 kPa (~50 psig) to about 34,480 kPa (~5000 psig), with about 1480 to about 7000 kPa preferred. The hydrogenation process can be conducted at temperatures from about 50° C. to about 180° C., preferably from about 65° C. to about 100° C.

Preferred catalysts for hydrogenating nitriles to amines comprise one or more elements from the series of transition metals, particularly useful are iron, cobalt, nickel, rhodium and combinations thereof. The hydrogenation catalyst may also comprise one or more elements in addition to the transition metals mentioned above, for example, elements of Group IA (including lithium, sodium and potassium), elements of Group IIA (including magnesium and calcium), titanium, elements of Group VI (including chromium, molybdenum and tungsten), elements of Group VIII (including palladium) and/or aluminum, silicon, boron and/or phosphorous. The hydrogenation catalyst can also be in the form of an alloy, including a solid solution of two or more elements.

The transition metal for hydrogenation can also be supported on an inorganic support such as alumina, magnesium oxide and combinations thereof. The metal can be supported on an inorganic support by any means known to one skilled in the art such as, for example, impregnation, co-precipitation, ion exchange, or combinations of two or more thereof. The metal can be reduced before the hydrogenation reaction by any means known to one skilled in the art such as, for example, pretreatment with hydrogen, formaldehyde or hydrazine.

The hydrogenation catalyst can be present in any appropriate physical shape or form. It can be in fluidizable forms, powders, extrudates, tablets, spheres or combinations of two or more thereof. The hydrogenation catalyst may be in sponge metal form, for example, the Raney® nickels and Raney® cobalts. The molar ratio of hydrogenation catalyst to feed can be any ratio as long as the ratio can catalyze the hydrogenation. The weight ratio of hydrogenation catalyst to feed is generally in the range of from about 0.0001:1 to about 1:1, preferably about 0.001:1 to about 0.5:1. If the catalytic element is supported on an inorganic support or is a portion of an alloy or solid solution, the catalytic element is generally present in the range of from about 0.1 to about 60, preferably about 1 to about 50, and most preferably about 2 to about 50 weight percent based on the total hydrogenation catalyst weight.

It will be appreciated that one skilled in the art will select the catalyst to optimize the rate of reaction, selectivity of reaction and the level of catalyst leaching. The preferred nitrile hydrogenation catalyst is a sponge metal type catalyst. The metallic component is iron, ruthenium, cobalt, nickel or combinations thereof. Commercially available catalysts of this type are promoted or un-promoted Raney® Ni or Raney® Co catalysts that can be obtained from W.R. Grace and Co. (Chattanooga, Tenn.), or alternative sponge metal catalysts available, for example, from Activated Metals Corporation (Sevierville, Tenn.) or Degussa (Parsippany, N.J.). A supported ruthenium catalyst may also be used.

The hydrogenation can optionally be conducted in the presence of a solvent. Suitable solvents include those known in the art as useful for hydrogenation reactions. Examples of these are amines, aliphatic alcohols, aromatic compounds, ethers, esters (including lactones), and amides (including lactams). Specific examples of solvents include: ammonia, toluene, tetrahydrofuran, methanol, ethanol, any isomeric propanol, any isomeric butanol and water. Preferred solvents include ammonia, and toluene. It will be appreciated that the solvent may serve to reduce the viscosity of the system to improve fluidity of the catalyst in the reaction vessel, as well as serve to remove the heat of reaction from the feed and products. The solvent may be present in a range of about 1% to about 75% by weight of the total reaction mixture, excluding the catalyst, preferably from about 10% to about 50%.

Optionally, a promoter may be used in the hydrogenation process to alter the rate of the reaction and/or alter the selectivity of the reaction. Suitable promoters include water, alkali or alkaline earth metal hydroxides, quaternary ammonium hydroxides, quaternary ammonium cyanides, quaternary ammonium fluorides, and combinations of these. Promoters may be present at from about 10 ppm to about 3% by weight of the total reaction mixture, excluding the catalyst, preferably from about 50 ppm to about 1.5%.

Having generally described this invention, a further understanding can be obtained by reference to certain specific examples, which are provided herein for purpose of illustration only and are not intended to be limiting.

EXAMPLES

Example 1-4

Hydrocyanation of Oleic Acid

A solution of catalyst was prepared by combining Ni(COD)$_2$ in toluene with a bidentate phosphite ligand in a ratio of Ni:ligand of 1:1.1. This solution was sampled into a reaction vessel. Oleic acid was added to the reaction vessel, the mole ratio of oleic acid to catalyst was 50:1. A solution of promoter was prepared by adding ZnCl$_2$ to acetonitrile. This promoter solution was added to the reaction mixture adjusting a mole ratio of Ni to Zn of 1:1. Hydrogen cyanide was added to the reaction vessel via vapor feed. The hydrogen cyanide reservoir was at room temperature while the reaction vessel was maintained at 50° C. The vapor feed was maintained for 24 hours after which time the samples were analyzed using standard GC methodology for products. The samples were first derivatized for analysis with a commercial reagent following established procedures (BSTFA, bistrimethylsilyltrifluoroacetamide, for typical use see for example Takao, Yuji et al. in Journal of Health Science (2003), 49(1), 88-90). All products were analyzed by GC-MS and NMR spectroscopy. Linearity is defined by the ratio of concentrations of the linear acid nitrile product to the sum of all acid nitrile products.

| Entry | Ligand | Conversion [%] | Linearity [%] |
|---|---|---|---|
| 1 | | 33 | 73 |
| 2 | | 52 | 75 |
| 3 | | 34 | 68 |
| 4 | | 31 | 63 |

Example 5

Hydrocyanation of Soy Bean Oil

In a 100 mL flask soy bean oil (30 g) was mixed with a toluene (16 g) solution of Ni(COD)$_2$ (0.31 g) and the following ligand (1.03 g):

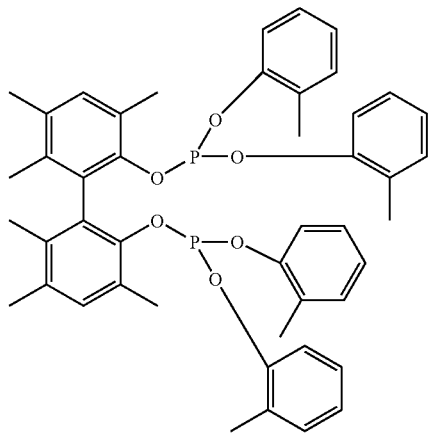

To this was added ZnCl$_2$ (0.045 g). A solution of hydrogen cyanide (2.85 g) in tulene (11.4 g) was prepared and added to the above mixture using a syringe pump. A feed rate of about 0.5 mL/hour was maintained at 70° C. The product composition was analyzed using LC-MS analysis on a Zorbax RX-C18 column (150×2.1, 5 μm) after the reaction was terminated: 70.1% conversion of soy bean oil to a mixture of products with 55% of MW=911 (addition of one equivalent of HCN), 35% MW=938 (addition of two equivalents of HCN) and 10% MW=965 (addition of three equivalents of HCN).

Example 6

Hydrogenation of Soybean Oil Nitrile

A solution of approximately 30 g of nitrile derived from soybean oil (comprising compound V) and 170 mL of toluene was prepared. The solution was charged to a 300 cc stirred pressure reactor with 3 g Raney® Co 2724 and 4.5 g water. The vessel was purged with hydrogen and then charged with hydrogen and heated to 75° C. at which point the pressure was adjusted to approximately 500 psig (3447 kPa) with hydrogen. The reaction proceeded for ten hours during which hydrogen was constantly replenished to maintain the operating pressure. The hydrogen was vented and the product recovered. Infrared and nuclear magnetic spectra of the product were consistent with the formation of the amine product (comprising compound VI) (IR: N—H 3350 cm$^{-1}$, C=O 1742 cm$^{-1}$).

Example 7

Hydrogenation of Oleic Acid Nitrile

To a 100 mL stirred pressure vessel were added 4.5 g of oleic acid derived nitrile (comprising compound (III) and isomers), 20 g tetrahydrofuran, 0.3 g Raney® Co 2724 and 0.3 g water. The vessel was purged with hydrogen and 21 g anhydrous ammonia was added. The vessel was then charged with hydrogen and heated to 100° C. at which point the pressure was adjusted to approximately 900 psig (6205 kPa) with hydrogen. The reaction proceeded for 335 minutes during which hydrogen was constantly replenished to maintain the operating pressure. The hydrogen and ammonia were vented and the product recovered. The product was sparingly soluble in common solvents such as tetrahydrofuran. Infrared and nuclear magnetic spectra of the product were consistent with the formation of the amine (IV). A probe mass spectrum further confirmed the identity of the desired product (mass 313.298).

Example 8

Hydrocyanation of Linoleic Acid

In a 500 mL flask linoleic acid (25 g, 0.09 mol) was mixed with a toluene (5 g) solution of Ni(COD)$_2$ (0.16 g, 0.6 mmol) and the following ligand (0.61 g, 0.8 mmol).

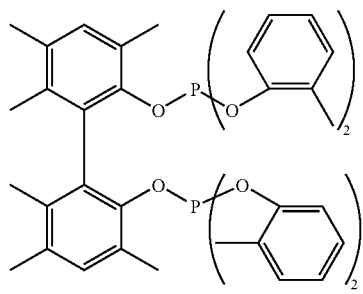

To this was added a solution of ZnCl$_2$ (0.09 g, 0.65 mmol) in acetonitrile (5 g). A solution of hydrogen cyanide (4.3 g, 0.16 mol) in acetonitrile (6.5 g) was prepared and added to the above mixture using a syringe pump. After a reaction time of 26 hours at 50° C. a conversion of 87% of linoleic acid to nitrile products was achieved. By GC (BSTFA method) a product mixture of 90% linoleic acid nitrile and 10% linoleic acid dinitrile was observed.

Example 9

Hydrogenation of Linoleic Acid Nitrile

To a 100 mL stirred pressure vessel were added 2.7 g of linoleic acid derived nitriles (comprising compound (VII) and isomers), 20 g tetrahydrofuran, 0.5 g Raney® Co 2724 and 1 g water. The vessel was purged with hydrogen and 20 g anhydrous ammonia were added. The vessel was then charged with hydrogen and heated to 85° C. at which point the pressure was adjusted to approximately 900 psig (6205 kPa) with hydrogen. The reactor conditions were maintained for 360 minutes, though a shorter time may have been sufficient. The hydrogen and ammonia were vented and the product recovered. A portion of the product was treated with excess bis(trimethylsilyl)trifluoroacetamide (BSTFA). Gas chromatography showed a major product peak accounting for 86% yield. A mass spectrum of the major peak from the product was consistent with formation of the amine (VII-A) (m/z=455, product plus two derivatizing trimethylsilyl groups).

Example 10

Hydrocyanation of 3-Pentenoic Acid

In a 500 mL flask 3-pentenoic acid (10 g, 0.1 mol) was mixed with a toluene (5 g) solution of Ni(COD)$_2$ (0.275 g, 1 mmol) and the following ligand (1.14 g, 1.35 mmol).

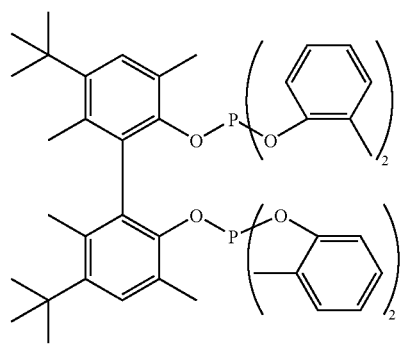

To this was added a solution of ZnCl$_2$ (0.15 g, 1.1 mmol) in acetonitrile (5 ml). A solution of hydrogen cyanide (5.4 g, 0.2 mol) in acetonitrile (8.1 g) was prepared and added to the above mixture using a syringe pump. The reaction mixture was maintained at 50° C. and the addition stopped after 18 hours. The product was analyzed after derivatization using BSTFA and a 50% conversion to cyano-pentanoic acid was observed.

Example 11-13 and Comparative Example 14

Hydrocyanation of 3-Pentenoic Acid

A solution of catalyst was prepared by combining Ni(COD)$_2$ in toluene with the phosphite ligand in a ratio of Ni:ligand of 1:1.1 if a bidentate ligand was used and in a ratio of Ni:ligand of 1:4.5 if a monodentate ligand was used. This solution was sampled into a reaction vessel. 3-Pentenoic acid was added to the reaction vessel, the ratio of 3-penteneoic acid to catalyst was 50:1. A solution of promoter was prepared by adding ZnCl$_2$ to acetonitrile, this promoter solution was added to the reaction mixture with a mole ratio of Ni to Zn of 1:1. Hydrogen cyanide was added to the reaction vessel by vapor feed of evaporating liquid hydrogen cyanide connected via feed tube to the reaction vessel. The hydrogen cyanide reservoir was at room temperature while the reaction vessel was maintained at 50° C. The vapor feed was maintained for 24 hours after which time the samples were analyzed using standard GC methodology. The samples were first derivatized for analysis with a commercial reagent following established procedures (BSTFA, bistrimethylsilyltrifluoroacetamide, for typical use see for example Takao, Yuji et al. in Journal of Health Science (2003), 49(1), 88-90). The products were analyzed by GC-MS and NMR spectroscopy. Linearity is defined as the ratio of concentrations of the 5-cyano-pentanoic acid isomer to the sum of all cyano-pentanoic acid isomers.

| Example | Ligand | Conversion [%] | Linearity [%] |
|---|---|---|---|
| 11 | | 76 | 93 |
| 12 | | 85 | 92 |
| 13 | | 79 | 91 |
| C. ex 14 | | no conversion | |

Various modifications, alterations, additions or substitutions of the process and compositions of this invention will be apparent to those skilled in the art without departing from the spirit and scope of this invention. This invention is not limited to the illustrative embodiments set forth herein, but rather is defined by the following claims.

What is claimed is:
1. A compound of formula III:

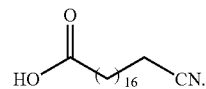

(III)

* * * * *